US011452430B2

(12) United States Patent
Almendros Carmona et al.

(10) Patent No.: US 11,452,430 B2
(45) Date of Patent: Sep. 27, 2022

(54) HOUSEHOLD APPLIANCE AND METHOD FOR CONTROLLING SAME

(71) Applicant: BSH Hausgeräte GmbH, Munich (DE)

(72) Inventors: Ismael Jesus Almendros Carmona, Pamplona (ES); Min Chen, Nanjing (CN); Beibei Wang, Nanjing (CN); Hailing Zhang, Nanjing (CN); Wei Wang, Nanjing (CN)

(73) Assignee: BSH Hausgeräte GmbH, Munich (DE)

( * ) Notice: Subject to any disclaimer, the term of this patent is extended or adjusted under 35 U.S.C. 154(b) by 267 days.

(21) Appl. No.: 16/609,758

(22) PCT Filed: Apr. 16, 2018

(86) PCT No.: PCT/IB2018/052622
§ 371 (c)(1),
(2) Date: Oct. 31, 2019

(87) PCT Pub. No.: WO2018/203163
PCT Pub. Date: Nov. 8, 2018

(65) Prior Publication Data
US 2020/0060504 A1    Feb. 27, 2020

(30) Foreign Application Priority Data
May 2, 2017   (CN) .......................... 201710300066.6

(51) Int. Cl.
*A47L 15/00*    (2006.01)
*D06F 58/46*    (2020.01)
(Continued)

(52) U.S. Cl.
CPC ....... *A47L 15/0036* (2013.01); *A47L 15/0034* (2013.01); *D06F 58/46* (2020.02);
(Continued)

(58) Field of Classification Search
CPC .................................................. A47L 15/0036
See application file for complete search history.

(56) References Cited

U.S. PATENT DOCUMENTS

2017/0350067 A1    12/2017   Choi

FOREIGN PATENT DOCUMENTS

| CN | 105999326 A | 10/2016 |
| CN | 106052292 A | 10/2016 |

(Continued)

OTHER PUBLICATIONS

International Search Report PCT/IB2018052622 dated Aug. 8, 2018.

*Primary Examiner* — Jason Y Ko
(74) *Attorney, Agent, or Firm* — Michael E. Tschupp; Andre Pallapies; Brandon G. Braun

(57) ABSTRACT

The present invention relates to a household appliance and a method for controlling same. The household appliance includes: at least one chamber for accommodating a to-be-processed object and at least one door for closing the chamber; a collection module, at least for collecting a time signal when the door is opened; a controller, connected to the collection module to receive and analyze the time signal generated by the collection module when the door is opened, count a high-frequency time segment when the door is opened in a predetermined time period T1, and generate a control signal for controlling an operation state of a function loading module; and the function loading module, connected to the controller to receive the control signal for controlling operation of the function loading module. Therefore, the present invention provides a household appliance with a new control method.

16 Claims, 5 Drawing Sheets

(51) Int. Cl.
   *D06F 103/38*   (2020.01)
   *A47L 15/46*   (2006.01)
   *D06F 103/40*   (2020.01)
   *D06F 105/52*   (2020.01)
   *D06F 105/56*   (2020.01)
   *D06F 33/44*   (2020.01)
   *D06F 105/62*   (2020.01)

(52) U.S. Cl.
   CPC ........... *A47L 15/46* (2013.01); *A47L 2401/26* (2013.01); *A61L 2202/122* (2013.01); *D06F 33/44* (2020.02); *D06F 2103/38* (2020.02); *D06F 2103/40* (2020.02); *D06F 2105/52* (2020.02); *D06F 2105/56* (2020.02); *D06F 2105/62* (2020.02)

(56) References Cited

FOREIGN PATENT DOCUMENTS

| | | |
|---|---|---|
| EP | 3135178 A1 | 3/2017 |
| JP | H01320039 A | 12/1989 |
| JP | H04273981 A | 9/1992 |

| | H1 | H2 | H3 | H4 | H5 | H6 | H7 | H8 | H9 | H10 | H11 | H12 | H13 | H14 | H15 | H16 | H17 | H18 | H19 | H20 | H21 | H22 | H23 | H24 |
|---|---|---|---|---|---|---|---|---|---|---|---|---|---|---|---|---|---|---|---|---|---|---|---|---|
| D1 | 0 | 0 | 0 | 0 | 1 | 1 | 0 | 1 | 0 | 0 | 1 | 1 | 1 | 0 | 0 | 1 | 0 | 1 | 1 | 1 | 1 | 0 | 0 | 0 |
| D2 | 0 | 0 | 0 | 0 | 0 | 1 | 1 | 1 | 0 | 0 | 0 | 1 | 1 | 0 | 0 | 0 | 1 | 1 | 0 | 0 | 1 | 1 | 0 | 0 |
| D3 | 0 | 0 | 0 | 0 | 0 | 1 | 1 | 0 | 0 | 0 | 0 | 1 | 1 | 0 | 0 | 0 | 0 | 1 | 1 | 1 | 0 | 0 | 0 | 0 |
| D4 | 0 | 0 | 0 | 0 | 1 | 1 | 1 | 0 | 0 | 0 | 0 | 1 | 1 | 0 | 0 | 0 | 0 | 0 | 1 | 0 | 1 | 1 | 0 | 0 |
| D5 | 0 | 0 | 0 | 0 | 0 | 1 |   | 0 | 1 | 0 | 0 | 1 | 0 | 0 | 0 | 0 | 1 | 1 | 1 | 0 | 1 | 0 | 0 | 0 |
| D6 | 1 | 0 | 0 | 0 | 0 | 1 |   | 1 | 1 | 0 | 0 | 0 | 0 | 1 | 1 | 0 | 1 | 1 | 0 | 0 | 0 | 0 | 0 | 0 |
| D7 | 0 | 0 | 0 | 0 | 0 | 0 | 1 | 1 | 0 | 0 | 0 | 1 | 0 | 1 | 0 | 0 | 0 | 0 | 1 | 1 | 1 | 1 | 0 | 0 |
| D8 | 0 | 0 | 0 | 0 | 1 | 0 | 1 | 0 | 0 | 0 | 1 | 1 | 1 | 0 | 0 | 1 | 1 | 1 | 1 | 0 | 1 | 1 | 0 | 0 |
| D9 | 0 | 0 | 0 | 0 | 1 | 1 |   | 1 | 1 | 0 | 1 | 1 | 1 | 0 | 0 | 0 | 0 | 1 | 0 | 0 | 0 | 1 | 0 | 0 |
| D10 | 0 | 0 | 0 | 0 | 0 | 1 | 1 | 1 | 0 | 1 | 0 | 1 | 0 | 0 | 0 | 0 | 1 | 1 | 1 | 0 | 0 | 0 | 0 | 0 |
| D11 | 0 | 0 | 0 | 1 | 0 | 0 | 1 | 1 | 0 | 0 | 1 | 0 | 0 | 0 | 0 | 1 | 1 | 1 | 0 | 1 | 0 | 0 | 0 | 0 |
| D12 | 0 | 0 | 0 | 0 | 0 | 1 |   | 0 | 0 | 0 | 0 | 1 | 1 | 1 | 0 | 0 | 1 | 1 | 1 | 1 | 1 | 1 | 0 | 0 |
| D13 | 0 | 0 | 0 | 0 | 0 | 1 | 1 | 1 | 1 | 0 | 0 | 1 | 0 | 0 | 0 | 1 | 1 | 1 | 1 | 0 | 0 | 0 | 0 | 0 |
| D14 | 0 | 0 | 0 | 0 | 1 | 1 | 1 | 0 | 0 | 0 | 0 | 1 | 0 | 0 | 0 | 0 | 1 | 1 | 0 | 0 | 1 | 0 | 0 | 0 |
| Sum | 1 | 0 | 0 | 1 | 5 | 11 | 9 | 8 | 4 | 1 | 4 | 12 | 7 | 2 | 1 | 3 | 6 | 12 | 12 | 6 | 8 | 7 | 0 | 0 |

FIG. 7

HOUSEHOLD APPLIANCE AND METHOD FOR CONTROLLING SAME

CROSS-REFERENCES TO RELATED APPLICATIONS

This application is the U.S. National Stage of International Application No. PCT/IB2018/052622, filed Apr. 16, 2018, which designated the U.S. and has been polished as International Publication No. WO 2018/203163 A1 and which claims the priority of Chinese Patent Application, Serial No. 20170300066.6, filed May 2, 2017, pursuant to 35 U.S.C. 119(a)-(d).

BACKGROUND OF THE INVENTION

The present inventions relates to a household appliance and a method for controlling same.

RELATED ART

The prior art Chinese patent CN105999326A discloses a sterilizing cabinet, inclining a cabinet body and a control panel disposed on the cabinet body. The control panel includes a control mainboard and a first key connected to the control mainboard. The first key is configured to receive a working time segment, preset by a user, of the sterilizing cabinet. The control mainboard is configured to determine whether a current time segment is in the preset working time segment, if yes, control the sterilizing cabinet to enter a sterilizing mode, and if not, control the sterilizing cabinet not to enter or exit from the sterilizing mode.

BRIEF SUMMARY OF THE INVENTION

An objective of the present inventions to resolve at least one technical problem existing in the prior art provide an improved household appliance.

The present invention relates to a household appliance, including: at least one chamber for accommodating a to-be-processed object and at least one door for closing the chamber; a collection module, at least for collecting a time signal when the door is opened; a controller, connected to the collection module to receive and analyze the time signal generated by the collection module when the door is opened, count a high-frequency time segment and/or a low-frequency time segment when the door is opened in a predetermined time period, and generate a control signal for controlling an operation state at a function loading module; and the function loading module, connected to the controller to receive the control signal for controlling operation of the function loading module.

The "high-frequency time segment when the door is opened is a predetermined time period" of the present invention is a time segment when the door is opened at a relatively high frequency it the predetermined time period. The "low-frequency time segment when the door is opened in a predetermined time period" is a time segment when the door is opened at a relatively low frequency in the predetermined time period.

By use the structure, the household appliance may learn use habits of a user, and count the high-frequency time segment anchor the low-frequency time segment when the door is opened ix the predetermined time period. In the low-frequency time segment, the user uses the household appliance at a relatively low frequency, and in the high-frequency time segment, the user uses the household appliance at a relatively high frequency. Therefore, the controller controls operation states of different timeline loading modules in the high-frequency time segment according to features of the different function loading modules, so that the household appliance is more intelligent and more humanistic, thereby improving user experience.

According to a schematic implementation of the present invention, the controller is configured to control the function loading module to operate in the low-frequency time segment, or not to operate or to be in a non-operation state in the high-frequency time segment.

In this way, the function loading module does not operate or is in a arm-operation state in the high-frequency time segment, and operates in the low-frequency time segment. The function loading module operates before the high-frequency time segment occurs and ends operation at least when the high-frequency time segment acmes. Therefore, the function loading module is prevented from operating in the high-frequency time segment, and the user is prevented from operating the function loading module when using the household appliance, so as to not only provide a clean environment of the chamber, but also improve user experience, thereby making the household appliance more intelligent.

According to a schematic implementation of the present invention, the controller is configured to control the function loading module to start to operate before the high-frequency time segment occurs and end operation when the high-frequency time segment occurs, or control the function loading module to operate in the low-frequency time segment.

In this way, the function loading module starts to operate before the high-frequency time segment occurs and ends operation when the high-frequency time segment occurs, to be prevented from operating in the high-frequency time segment, and prevent operation of the function loading module from affecting use experience of the user when the user uses the household appliance, so as to not only provide a clean environment of the chamber, but also improve user experience, thereby making the household appliance more intelligent.

According to a schematic implementation of the present invention, the function loading module includes a sterilizing module and/or a drying module, configured to perform sterilizing and/or drying on the to-be-processed object.

In this way, the sterilizing module and/or the drying module operate in the low-frequency time segment, or start to operate before the high-frequency time segment occurs and end operation when the high-frequency time segment occurs. The sterilizing module and/or the drying module do not operate or are in a non-operation state in the high-frequency time segment, to prevent the user from operating the sterilizing module and/or the drying module when the user rises the houses millrace, thereby improving user experience.

According to a schematic implementation of the present invention, the function loading module includes a healing module, configured to perform healing on the to-be-processed object.

In this way, the healing module operates in the low-frequency time segment, or starts to operate before the high-frequency time segment occurs and ends operation when the high-frequency time segment omits. The object n the chamber is heated. When the user uses the household appliance, the object in the chamber has a particular temperature, thereby improving user experience. The healing module does not operate or is in a non-operation state a the high-frequency time segment, to prevent the user from operating the heating module when the user uses the household appliance, thereby finder improving user experience.

According to a schematic mentation of the present invention, duration of operation of the function loading module for one period is T, and the function loading module starts to operate after the duration T before the high-frequency time segment occurs.

In this way, the fraction loading module starts to run after the duration T before the high-frequency time segment occurs, and just ends operation when the high-frequency time segment occurs. In this way, the function loading module is not only prevented firm operating in the high-frequency time segment, but also just ends when the high-frequency time segment occurs, thereby saving time and mantes while earning the performance.

According to a schematic implementation of the present invention, the controller is configured to receive and analyze the time signal generated by the collection module when the dory is opened, and count an average line segment when the door is opened in the predetermined time period, where when a time segment is greater than the average time segment by a preset multiple A, the time segment is the high-frequency time segment.

According to a schematic implementation of the present invention, the predetermined time period includes last N units of time, the collection module collects time signals when the door is opened in the last N units of time, and the controller receives and analyzes the collected time signals to count a high-frequency time segment and/or a low-frequency time segment of using the household appliance per unit of time.

By using the structure, the high frequency time segment and/or the low-frequency time segment when the door is opened in modular time, that is, the high-frequency time segment and/or the low-frequency time segment of using the household appliance, may be counted.

According to a schematic implementation of the present invention, the unit of time is day.

According to a schematic implementation of the present invention, one unit of time is divide into M unit intervals, the collection modish collects a time signal when the door is opened in each unit interval, and continuously collects time signals in the last N units of time; and the controller receives and analyzes the collected time signals to count high-frequency and intend and low-frequency intervals per unit of time; the high-frequency time segment is composed of fie high-frequency unit intervals, and the low-frequency time segment is composed of the low-frequency intervals. By using the structure, the high-frequency unit intervals in the high-frequency time segment and the low-frequency intervals in the low-frequency time segment may further be counted.

According to a schematic implementation of the present invention, the household appliance is a sterilising cabinet, a dish washer, or a washing machine.

To achieve the foregoing objective, the present invention further provides a method for controlling a household appliance, where the household appliance includes at least ore chamber for accommodating a to-be-processed object and at least one door for closing the chamber 1 and the control method includes the following steps:

a). collecting a time signal when the door is opened in a predetermined time period;

b). receiving and analyzing, by a continuer, the collected time signal when the door is opened to obtain a high-frequency time segment and/or a low-frequency dine segment when the door is opened in the predetermined time period, and generating a control signal; and c). receiving, by a function baring module, the control signal, where the control signal is used far controlling operation of the function loading module.

By using the method, the high-frequency time segment and/or a law-frequency time segment when the door is opened in the predetermined time period may be courted, to obtain that in the high-frequency time segment, the user uses the household appliance at a relatively high frequency, and in the low-frequency time segment, the user uses the household appliance at a relatively low frequency, and use habits of the user are learned. Therefore, the controller controls operation states of different function laming modules n the high-frequency time segment and/or the low-frequency time segment according to features of the different function loading modules, so that the household appliance is mere indigent and mine humanistic, thereby improving user experience.

According to a schematic implementation of the present invention, the control method fluffier includes step d), determining whether an interval between current time and next operation time of the function loading module is in a predetermined time period, and if yes, controlling the function loading module not to operate.

Therefore in the predetermined time period, the function loading module operates only once, to be prevented from repeatedly operatic in a time segment other than the high-frequency time segment, thereby saving time and consumption while ensuring the performance.

According to a schematic implementation of the present invention, step b) includes: receiving and analyzing, by the controller, the time signal generated by the collection module when the door is opened, and counting an average time segment when the door is opened is the predetermined time period, where when a time segment is greater than the average time segment by a preset multiple A, the line segment is the high-frequency time segment.

According to a schematic implementation of the present invention, in step b), the predetermined time period includes last N units of time, the collection module collects time signals when the door is opened it the last N twits of time, and the co liar receives and analyzes the collected time signal to count a high-frequency time segment and/or a low-frequency time segment when the door is opened per unit of time.

By using the method, the high-frequency time segment when the door is opened in modular time, that is, the high-frequency time segment and/or the low-frequency time segment of using the household appliance, may be counted.

According to a schematic implementation of the present invention, one unit of time is divide into M unit intervals, the collection module collects a time signal when the door is opened in each unit interval, and continuously collects time signals in the last limits of line; and the controller receives and analyzes the collected time signals to count high-frequency intervals and low-frequency intervals in the high-frequency time segment per unit of time; fire high-frequency time segues composed of the high-frequency intervals, and the low-frequency time segment is composed of the low-frequency intervals.

By using the method, the high-frequency intervals m the high-frequency the segment and the low-frequency ovals may be counted.

According to a schematic implementation of the present invention; characterized is that, step c) includes: the controller being configured to determine whether a current time segment is in the high-frequency time segment of the household appliance, if yes, control the function loading module not to operate or to be in a non-operation state; and if not, control the function loading module to operate.

By using the method, the function loading module does not operate or is in a non-operation slate IL the high-icy time segment, and operates before the high-frequency time segment occurs and ends operation at least when the high-frequency time segment occurs, to be prevented from operating is the high-frequency time segment, and prevent the user from operating. The function loading module when the user uses the household appliance, so as to make the household appliance mare intelligent, thereby improving user experience.

According to a schematic implementation of the present invention, characterized in that, step e) includes: the controller being configured to determine whether a current time segment is in the low-frequency time segment of the household appliance, if yes, cresol the function loading module to operate, and if not, control the function loading module not to operate or to be is a non-operation state.

By using the method, the function loading module operates in the low-frequency time segment, to be prevented from operating is the high-frequency time segment, and prevent the user from operating the function boding module when the user uses the household appliance, so as to make the household appliance more intelligent, thereby improving user experience.

According to a schematic implementation of the present invention, step c) includes: controlling by the contra, the function loading module to operate before the high-frequency time segment acmes and end operation when the high-frequency time segment occurs.

By using the method, the function loading module starts to operate before the high-frequency time segment occurs and ends operation when the high-frequency time segment occurs, to be prevented from operating in the high-frequency time segment, and prevent operation of the function loading module from affecting use experience of the user when the user uses the household appliance, so as to make the household appliance more intelligent, thereby improving user experience.

According to a schematic implementation of the present invention, the function loading module includes a sterilizing module and/or a drying module.

In the way, the steaming module and/or the drying module start to operate before the high-frequency time segment occurs and end operation when the high-frequency time segment occurs. The sterilizing module and/or the drying module do not operate or are in a non-operation state it the high-frequency time segment, to prevent the user from operating the sterilizing module and/or the drying module when the user uses the household appliance, thereby improving laser experience.

According to a schematic implementation of the present invention, the function loading module includes a sterilizing module and/or a drying module.

In this way, the heating module starts to operate before the high-frequency time segment occurs and ends operation when the high-frequency time segment occurs. The heating module dues not operate or is it a non-operation state in the high-frequency time segment, to prevent the user from operating the heating module when the user uses the household appliance, thereby improving user experience.

BRIEF DESCRIPTION OF THE DRAWINGS

FIG. 7 is a table for counting the high-frequency time segment oft household appliance in the predetermined time period according to an embodiment of the present invention.

DETAILED DESCRIPTION

To further learn the objective, structure, features, and functions thereof of the present invention, detailed description is provided below with reference to the embodiments.

Figure 1:
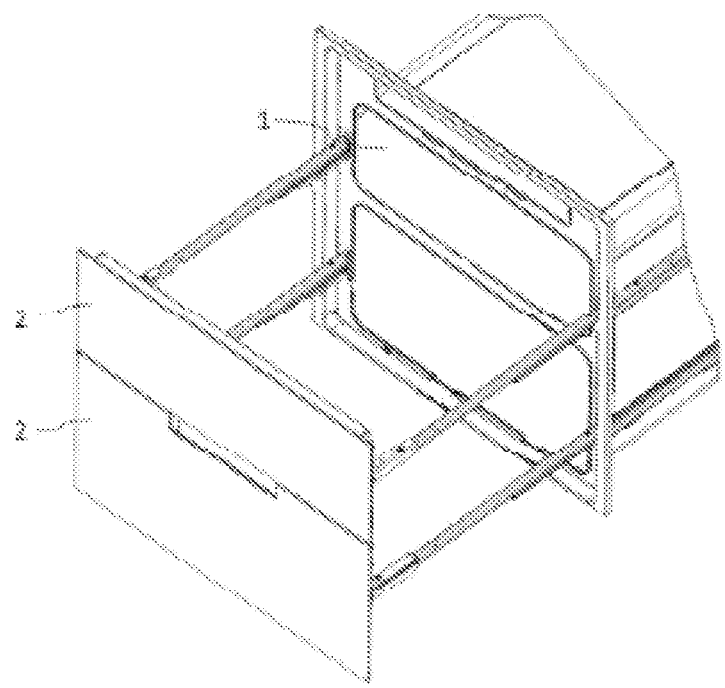
FIG. 1 is a schematic diagram of an overall structure of an embodiment of a household appliance of the present invention.

As shown in FIG. 1, a household app race includes at least we chamber 1 for accommodating a to-be-processed object and at least one door 2 for closing the chamber 1. The household appliance may be a sterilizing cabinet a dish washer, or a washing machine.

Figure 2:
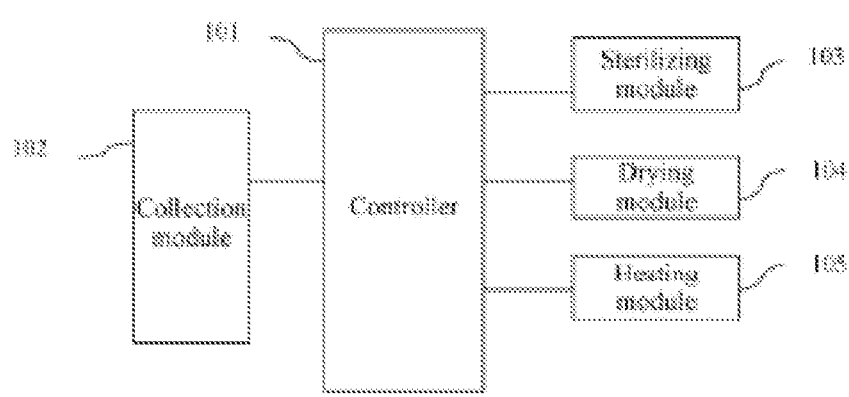
FIG. 2 is an electrical principle diagram of an embodiment of a household appliance of the present invention.
Figure 3:
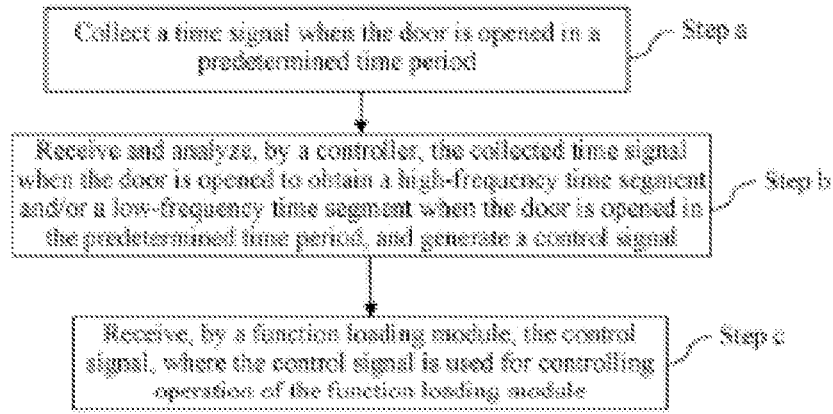
FIG. 3 is a flowchart of an embodiment of a method for controlling a household appliance of the present invention.
Figure 4:
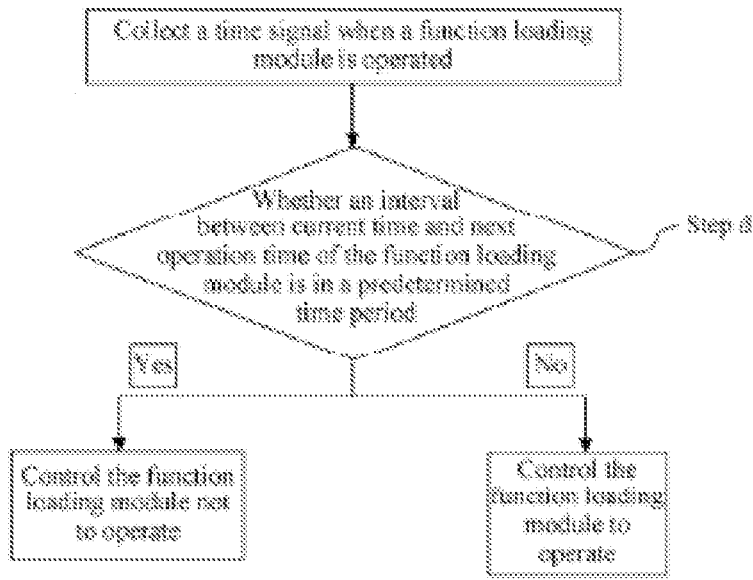
FIG. 4 is a flowchart of another embodiment of a method for controlling a household appliance according to an embodiment of the present invention.
Figure 5:
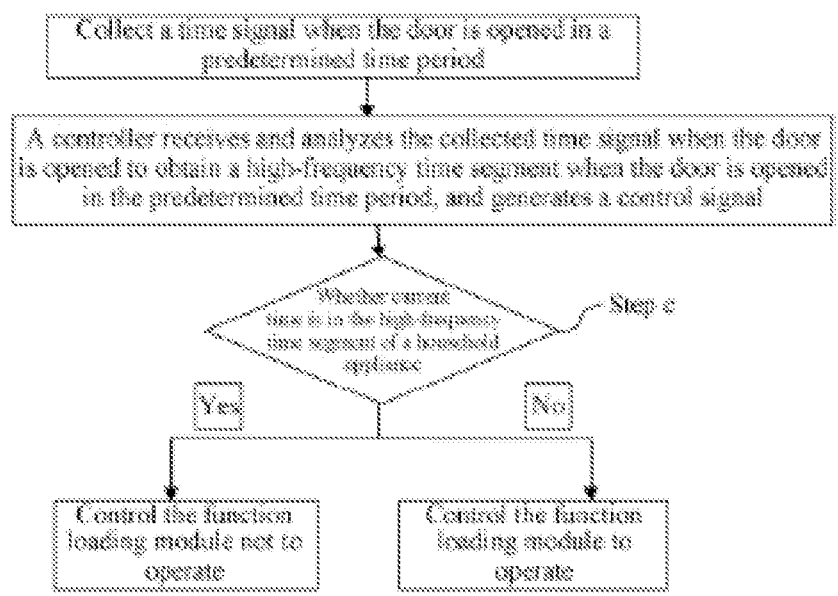
FIG. 5 is a flowchart of still another embodiment of a method for controlling a household appliance according to an embodiment of the present invention.

As shown in FIG. 2, the household appliance further includes a controller 101 and a collection module 102 connected to each other. The collection module 102 is used at least for collecting a time signal when the door 2 is opened.

The controller 101 receives and analyzes the time signal generated by the collection module 102 when the door 2 is opened, counts a high-frequency time segment and/or a low-frequency time segment when the door 2 is opened in a predetermined time period T1, and generates a control signal for controlling an operation state of a function loading module.

The household appliance further includes the function loading module fix performing corresponding processing on the to-be-processed object in the chamber 1. The function loading module is connected to the controller 101 to receive the control signal for controlling operation of the function loading module.

The function loading module includes at least a sterilizing module 103, a drying module 104, and a heating module 105. The sterilizing module 103 is configured to perform sterilizing on the to-be-processed object in the chamber 1. The drying module 104 is configured to perform drying on the to-be-processed object in the chamber 1. The heating module 105 is configured to heat the to-be-processed object is the chamber 1. The heating module 105 iodides a heating element and a fan. The fan delivers hot air heated by the heating element into the chamber 1.

First, a high-frequency time segment and a low-frequency line segment of mug the household appliance are counted by learning behavioral habits of a user.

The controller 101 counts, in this way, the high-frequency time segment when the door 2 is opened it a predetermined time period T1: the predetermined time period T1 includes last N units of time, and then one unit of times divided into M unit intervals. The collection module 102 collects a time signal when the door 2 is opened in each unit interval, and continuously collects time signals in the last N units of time. The controller 101 receives the time signals of the collection module 102, and cowls the nimbler of times when the door 2 is opened in each unit interval in the last N units of time, to obtain H1 unit intervals in which the door 2 is opened for the largest number of times in the last N units of time, that is, high-frequency unit intervals. The high-frequency time segment is formed by these high-frequency unit intervals. In addition, H2 unit intervals with lowest use frequencies are counted as low-frequency intervals. The low-frequency time segment is formed by these low-frequency intervals. Therefore, the high-frequency time segment and the low-frequency time segment when the door 2 is ripened in the predetermined time period T1 are obtained.

In an embedment, an average time segment when the doer 2 is opened it the predetermined time period T1 is counted, and when a time segment is greater than the average time segment for a preset multiple A, the time segment is the high-frequency time segment.

The door 2 of the household appliance is usually opened when the user opens the household appliance, that is, when the user uses the household appliance. The high-frequency time segment when the door 2 is opened in the predetermined time period T1 is the high-frequency time segment of using the household appliance. The low-frequency time segment when the door 2 is opened it the predetermined time period T1 is the low-frequency time segment of using the household appliance. Therefore, the high-frequency time segued and the low-frequency time segment of using the household appliance are counted by learning the behavioral habits ante user.

In a specific implementation, the predetermined time period, the unit of time, and the unit interval may be set according to actual needs. For example, it an embodiment, the omit of time is day, and the unit interval is hour. An embodiment of counting the high-frequency time segment is described below.

Figure 6:
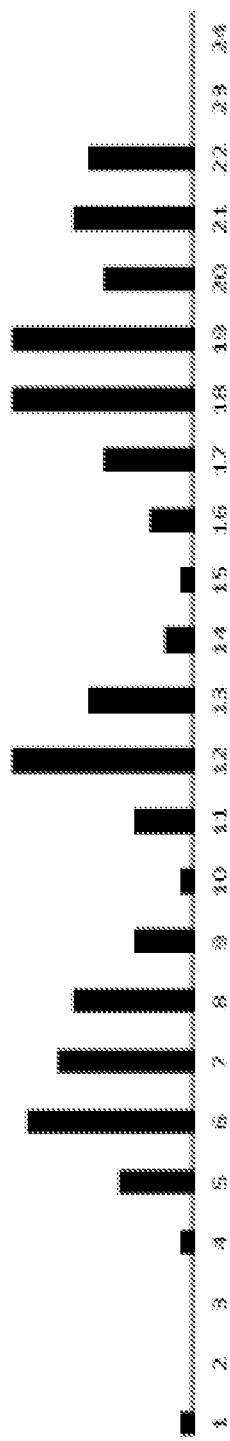
FIG. 6 is a chart of counting the high-frequency time segment of the household appliance in the predetermined time period according to an embodiment of the present invention.

Referring to FIG. 7 and FIG. 6, FIG. 7 and FIG. 6 are me embodiment of counting the high-frequency time segue of the household appliance in the predetermined time period T1. There are other counting methods.

Referring to FIG. 7 and the bide in FIG. 6, the predetermined time period T1 is 14 days, the unit of time is day, the unit interval is hour, and 1 day is divided into 24 hours. Upon an action of opening or closing the door 2, the collection module 102 sends a collection signal and feeds back the collection signal to the contoller 101, records whether the door 2 is opened it each how and marks a result in the interval, and continuously counts for 14 days. Three intervals with lowest use frequencies are filtered as the low-frequency time segment. H intervals with highest use frequencies are filtered as the high-frequency time segment. On the fifteenth day, the high-frequency time segment and the leaf-frequency time segment are counted based on data of the first day to the fourteenth day, and an the sixteenth day, the high-frequency time segment and the low-frequency time segment are counted based an data of the second day to the fifteenth day, thereby ensuring that the result is based an recent behaviors of the user.

If operation time of the function loading module is 2 hours, suns of frequencies of adjacent two intervals may be synchronously collected, and three intervals with lowest frequencies are also filtered as the low-frequency time segment, and H intervals with highest frequencies are filtered as the high-frequency time segment.

H1 and H2 may be selected according to needs. In one embodiment H1 and 112 are 1, in another embodiment, H1 and 112 are 2, and in sill another embodiment, H1 and H2 are 3.

The controller 101 is configured to control the function loading module to start to operate before the high-frequency time segment occurs and end operation when the high-frequency time segment occurs, that is, control the function loading module not to operate or to be in a non-operation state in the high-frequency time segment. The cater 101 further controls the function loading module to operate in the low-frequency time segment. In an embodiment, duration of operation of function loading module for ore period is T, and the function loading module starts to operate after the duration T before the high-frequency time segment occurs.

Therefore, the household appliance may learn use habits of the user to count the high-frequency time segment and the low-frequency time segment when the door 2 is opened in the predetermined time period. In the high-frequency time segment, the user uses the household appliance at a relatively high frequency, and in the low-frequency time segment, time user uses the household appliance at a relatively boar frequency. The controller 101 controls the function loading module not to operate or to be in a non-operation state in the high-frequency time segment, and controls the function loading module to operate it the low-frequency time segment, to prevent the function haft module firm operating in the high-frequency time segment, and prevent the user from operating the function boding module when the user uses the household appliance, so as to make the household appliance mare intelligent, thereby improving user experience.

The present invention further provides a method for controlling a household appliance. The household appliances stated above, and the control method includes the following steps:

a). collecting a time signal when the door 2 is opened in a predetermined time period;

b). receiving and analyzing, by a controller 101, the collected time signal when the door 2 is opened to obtain a high-frequency time segment and/or a low-frequency time segment when the door 2 is opened in the predetermined time period, and generating a control signal; and c). receiving, by a function loading module, the control signal, where the control signals used far controlling operation of the function loading module.

A method for counting the high-frequency time segment of the household appliance is descried above. Details are not described herein again.

In an embodiment, step c) includes: the controller 101 being configured to determine whether a current time segment is in the high-frequency time segment of the household appliance, if yes, control the function loading module not to operate or to be in a non-operation state; and if not, control the function loading module to operate.

Therefore, the function loading module does not operate in the high-frequency time segment, to prevent the user from operating the function loading module when the user uses the household appliance, thereby providing a clean environment of the chamber 1 and good user experience.

In another embodiment step c) includes: the controller 101 being configured to determine whether a current time segment is in the low-frequency time segment of the household appliance, if yes, control the function loading module to operate, and if not, control the function loading module not to operate or to be in a non-operation state. Therefore, the household appliance operates in the low-frequency time segment.

In another embodiment step c) includes: controlling, by the controller 101, the function loading module to operate before the high-frequency time segment occurs and end operation when the high-frequency time segment occurs.

Further, the control method further includes step d), determining whether an interval between current time and next operation line of the function loading module is in a predetermined time period, and if yes, controlling the function loading module not to operate.

Therefore, in the predetermined time period T1, the function loading module operates only once, to be prevented from repeatedly operating in a time segment other than the high-frequency time segment, thereby saving line and consumption whale ensuring the performance.

In the present invention, by automatically learning behavioral habits of a user by the household appliance, the high-frequency time segment and the low-frequency time segment of using the household appliance by the user are counted. The function loading module is controlled to operate in the low-frequency time segment, and stop operation in the high-frequency time segment, so that the user is prevented from operating the function loading module when using the household appliance, thereby providing a clean environment of the chamber 1 and good user experience, and making the household appliance more intelligent. In addition, the function loading module is controlled to operate once in a particular time period, to be prevented from repeatedly operating, thereby saving time and energy consumption while ensuring the performance.

The present invention is described through the foregoing related embodiments. However, the foregoing embodiments are merely examples of implementing the present invention. It should be noted that the disclosed embodiments do not limit the scope of the present invention. Instead, changes and modifications made without departing from the sprit and scope of the present invention shall fall within the protection scope of the present invention.

What is claimed is:

1. A household appliance, comprising:
   a chamber accommodating an object;
   a door for closing the chamber;
   a collection module configured to collect a time signal when the door is opened;
   a controller connected to the collection module and configured to
   receive and analyze the time signal collected by the collection module when the door is opened,
   count a high-frequency time segment or a low-frequency time segment when the door is opened in a predetermined time period, and
   generate a control signal in response to the analysis of the collected time signal; and
   a function loading module connected to the controller and receiving from the controller the control signal for controlling operation of the function loading module.

2. The household appliance of claim 1, wherein the household appliance is a sterilizing cabinet, a dish washer, or a washing machine.

3. The household appliance of claim 1, wherein the controller is configured to control the function loading module to operate in the low-frequency time segment, or to not operate or to be in a non-operation state in the high-frequency time segment.

4. The household appliance of claim 1, wherein the controller is configured to control the function loading module to start to operate before the high-frequency time segment occurs and to end operation when the high-frequency time segment occurs.

5. The household appliance of claim 1, wherein the function loading module comprises at least one module selected from the group consisting of a sterilizing module configured to perform sterilization on the object, a drying module configured to perform drying on the object, and a heating module configured to perform heating on the object.

6. The household appliance of claim 1, wherein a duration of one period of operation of the function loading module is T, and wherein the function loading module starts to operate after the duration T and before the high-frequency time segment occurs.

7. The household appliance of claim 1, wherein the time signal received and analyzed by the controller is an average time segment, and wherein a time segment that is greater than the average time segment by a preset multiple is defined as the high-frequency time segment.

8. The household appliance of claim 1, wherein the predetermined time period comprises last N units of time, said collection module collecting time signals when the door is opened in the last N units of time, with the controller receiving and analyzing the collected time signals to count a high-frequency time segment or a low-frequency time segment of per-unit-of-time-use of the household appliance.

9. The household appliance of claim 8, wherein a single unit of time is divided into M unit intervals, with the collection module collecting a time signal each time the door is opened in the M unit intervals, and continuously collecting time signals in the last N units of time; said controller receiving and analyzing the collected time signals to count per unit of time in the high-frequency time segment high-frequency unit intervals as part of the high-frequency time segment and low-frequency unit intervals per unit of time as part of the low-frequency time segment.

10. A method for controlling a household appliance having a chamber for accommodating an object and a door for closing the chamber, the method comprising:
    with a collection module, collecting a time signal when the door is opened in a first predetermined time period;
    with a controller, receiving and analyzing the collected time signal to obtain a high-frequency time segment and/or a low-frequency time segment when the door is opened in the first predetermined time period;
    generating a control signal in response to the analysis of the collected time signal; and
    transmitting the control signal to a function loading module for controlling operation of the function loading module.

11. The method of claim 10, further comprising:
    determining whether an interval between a current time and a next operation time of the function loading module is in a second predetermined time period, and when the interval is in the second predetermined time period, controlling the operation of the function loading module to be inoperative.

12. The method of claim 10, wherein receiving and analyzing the time signal generated by the collection module when the door is opened includes counting a duration of an average time segment when the door is opened in the first predetermined time period, and wherein when a duration of a time segment is greater than the duration of the average time segment by a preset multiple, the time segment is the high-frequency time segment.

13. The method of claim 10, wherein the first predetermined time period comprises last N units of time, with time signals being collected when the door is opened in the last N units of time, wherein the controller receives and analyzes the collected time signals to count per unit of time a high-frequency time segment or a low-frequency time segment when the door is opened.

14. The method of claim 13, further comprising:
dividing one unit of time into unit intervals,
collecting a time signal when the door is opened in each of the unit intervals, and
continuously collecting time signals in the last N units of time; and
analyzing the collected time signals to count in the high-frequency time segment high-frequency unit intervals per unit of time as part of the high-frequency time segment and low-frequency unit intervals per unit of time as part of the low-frequency time segment.

15. The method of claim 10, wherein the controller controls operation of the function loading module by
determining whether a current time segment is in the high-frequency time segment or the low-frequency time segment, and
when the current time segment is in the high-frequency time segment, controlling the function loading module not to operate or to be in a non-operation state; and
when the current time segment is in the low-frequency time segment, controlling the function loading module to operate.

16. The method of claim 10, wherein the controller controls operation of the function loading module by operating the function loading module before the high-frequency time segment occurs and end operation of the function loading module when the high-frequency time segment occurs.

* * * * *